United States Patent [19]
Cutter

[11] 4,416,022
[45] Nov. 15, 1983

[54] PRISM LIGHT-LINE SYSTEM

[75] Inventor: James W. Cutter, Hollister, Calif.

[73] Assignee: Litton Industrial Products, Inc., Beverly Hills, Calif.

[21] Appl. No.: 362,807

[22] Filed: Mar. 29, 1982

[51] Int. Cl.³ .............................................. A61B 6/08
[52] U.S. Cl. .................................... 378/206; 378/207
[58] Field of Search ....................... 378/205, 206, 207

[56] References Cited

U.S. PATENT DOCUMENTS 2,806,146 9/1957 Thompson ........................... 378/206
2,887,586 5/1959 Reininger ............................. 378/206
3,863,073 4/1973 Wagner.

FOREIGN PATENT DOCUMENTS 1021814 12/1952 France ................................ 378/206

Primary Examiner—Alfred E. Smith
Assistant Examiner—T. N. Grigsby
Attorney, Agent, or Firm—John M. Haurykiewicz; Robert E. Lowe; Walter R. Thiel

[57] ABSTRACT

A cylindrical lens-prism light-line generating apparatus utilizing a slit-type aperture provides for origination, collimation and projection of a light-line which cooperates with a light localizer beam in aid of aligning an X-ray beam path preparatory to radiography.

12 Claims, 8 Drawing Figures

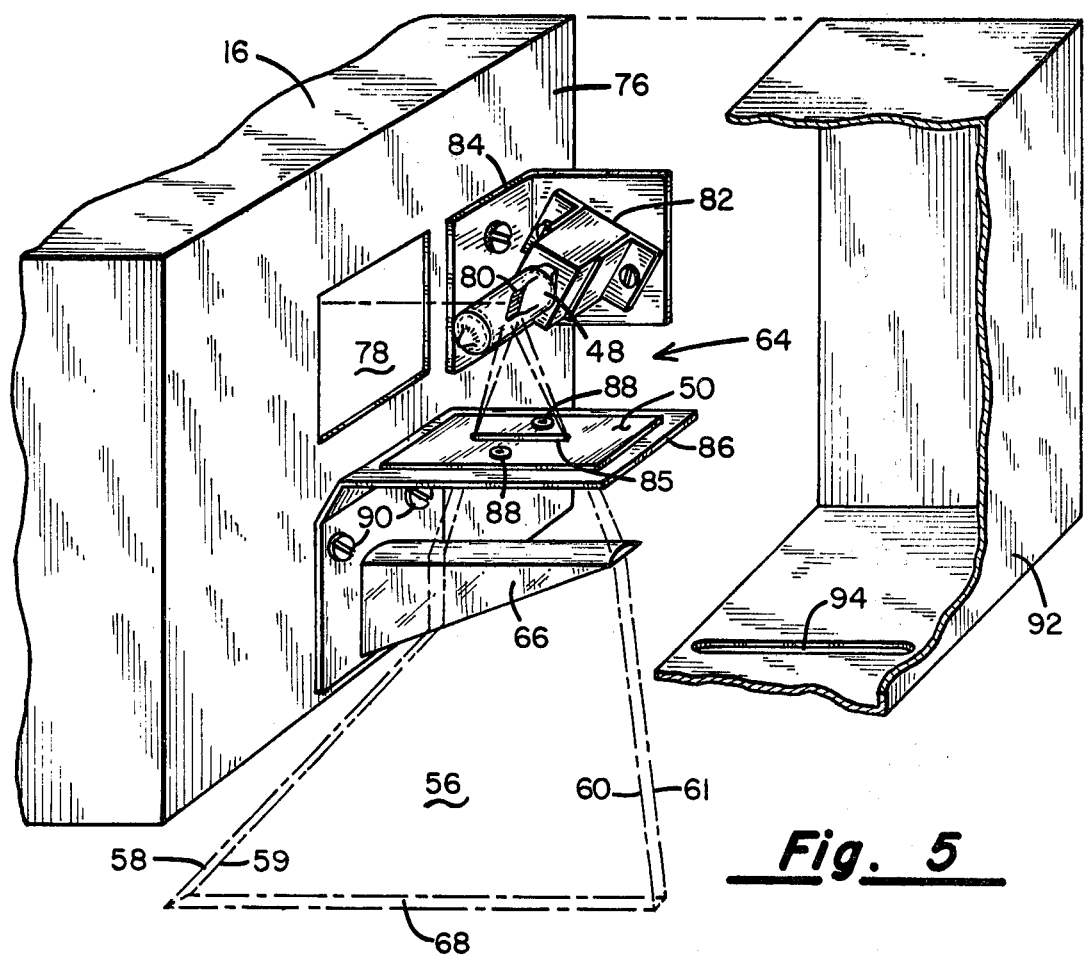
Fig. 5
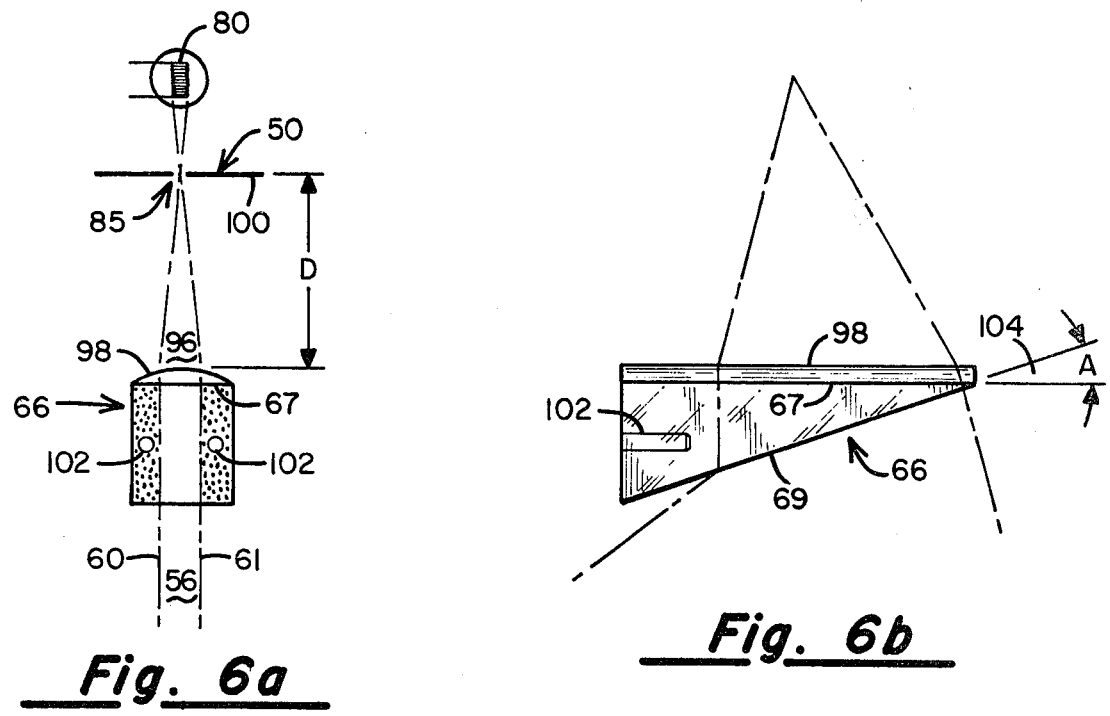
Fig. 6a
Fig. 6b

PRISM LIGHT-LINE SYSTEM

BACKGROUND OF THE INVENTION

X-ray radiography, the taking of photographs by a form of radiation other than light (more specifically X-rays) is a useful medical diagnostic and therapeutic technique. At the same time such radiation used for radiography must be carefully controlled and limited to that necessary, particularly when X-rays are utilized for the treatment of human beings. The Bureau of Radiological Health (BRH) has promulgated Federal Regulations governing the performance of equipment utilized for such purposes.

In the past, attempts to refine the design of X-ray apparatus have resulted in the development of systems utilizing visible light beams to simulate and correspond to the coverage of the invisible X-ray beam so as to enable proper placement and coverage during X-ray radiography to comply with BRH regulations.

Attemps have been made in the past to provide an aid in aligning the film with the X-ray beam by having an optical system project two beams of light to aid in aligning film with the X-ray beam. The first beam of light, called a light localizer, corresponds in cross-sectional area in the film plane with the cross-sectional area of the invisible X-ray beam. Furthermore, to comply with BRH regulations, the X-ray beam cross-sectional area cannot overlap beyond the film area. The second visible light beam utilized in the past consisted of a relatively short line or stripe of light directed to an index mark on the handle of the X-ray film cassette tray. Because of the short length of this beam, it was found necessary to position the X-ray head at a fixed distance from the film in order for the beam to strike the indicator. This has been found to be a hindrance to the flexibility and speed and ease of operation of X-ray equipment.

SUMMARY OF THE INVENTION

In order to further the objectives of safe and efficient operation, the present invention provides for a light-line or stripe of light to more readily permit visual alignment of an X-ray source with an object to be radiographed. The system for producing the improved light-line of this invention utilizes a source of visible light, a slit aperture, and means to collimate and project a narrow light-line whose length is greatly in excess of that producible by conventional means.

According to further aspects of this invention, the means to collimate and project the light include a cylindrical lens and prism.

According to another aspect of this invention, a light-line is provided having a length at least as long as one edge dimension of a projected image of the rectangular cross-section of the light localizing beam.

BRIEF DESCRIPTION OF THE DRAWINGS

FIG. 5 is an enlarged perspective view of a preferred embodiment of the light-line generating apparatus of this invention.

FIG. 6a is a simplified view of the apparatus of FIG. 5.

FIG. 6b is a side view of the preferred cylindrical lens-prism optical element of this invention.

DETAILED DESCRIPTION

Figure 1:
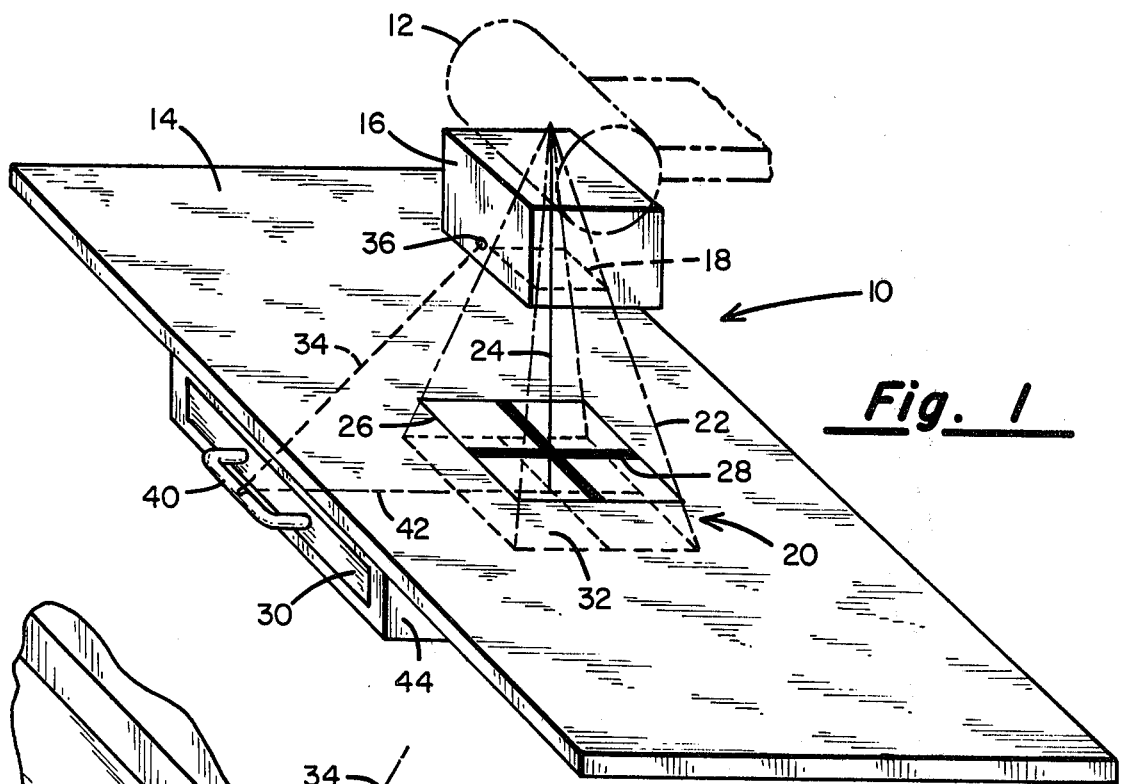
FIG. 1 is a perspective view of X-ray apparatus illustrating the light localizer beam.

Referring to FIG. 1, an X-ray radiography apparatus is shown generally at 10. More particularly, the apparatus includes a source of X-rays shown in phantom in its housing 12 positioned above an X-ray table 14 upon which an object to be radiographed is ordinarily placed in a manner well known. An X-ray collimator 16 is shown in outline and is attached to X-ray source housing 12. A collimator 16 provides an adjustable aperture 18 which determines the angle of divergence of X-rays emitted from source 12.

It is to be understood that an X-ray collimator functions in a manner different than an optical collimator. As is commonly used and understood in the X-ray equipment industry, an X-ray collimator "collimates" an X-ray beam by providing an aperture, itself transparent to X-rays, but surrounded and defined by material impervious to X-rays. Such an aperture, when placed in the path of a diverging X-ray beam will control the angle of divergence. This is in contrast to and is to be distinguished from the commonly understood principle of optical collimation (used hereinafter with respect to the light-line system of this invention). Optical collimation refers to the effect of utilizing refraction of visible light to approach or obtain parallelism of boundaries of a visible light beam as it passes through an optical system. Refraction refers to the deflection or bending of a beam of light as it passes obliquely from one optical medium into another.

Because X-ray radiation is invisible, collimator 16 is ordinarily provided with a visible light optical system to project a beam of light which corresponds to the X-ray beam path. Such a visible light path or light localizer and its associated projected image is shown generally at 20. Light localizer beam 22 is a three-dimensional pyramidal light beam centered on axis 24 which projects a rectangular cross-section image 26 when axis 24 is perpendicular to table 14. Projected image 26 is further characterized by shadows 28 bisecting image 26. The film to be used in the radiographic procedure is located in a cassette (not shown) and centered in a cassette tray 30 in a film plane 32 below the plane of the upper surface of table 14. Collimator 16 will limit the area exposed to X-ray radiation to the cross-section of the beam 22.

Figure 1A:
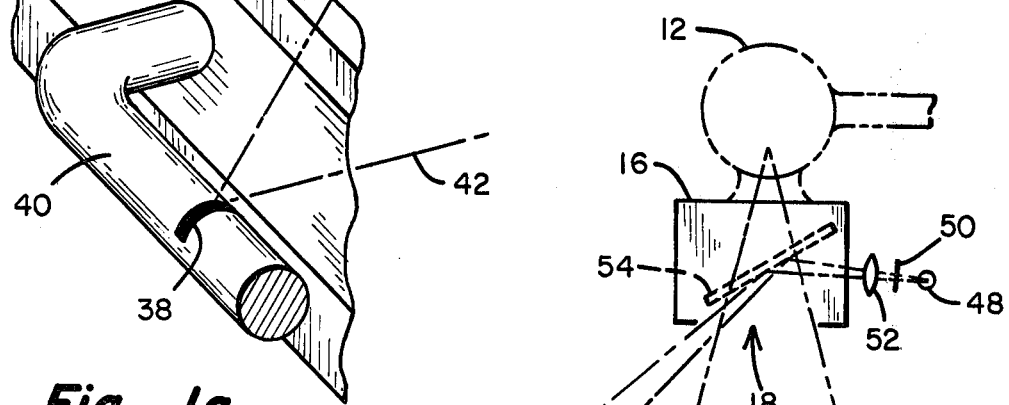
FIG. 1a is a detailed view showing the X-ray film holder center line indicator.
Figure 2:
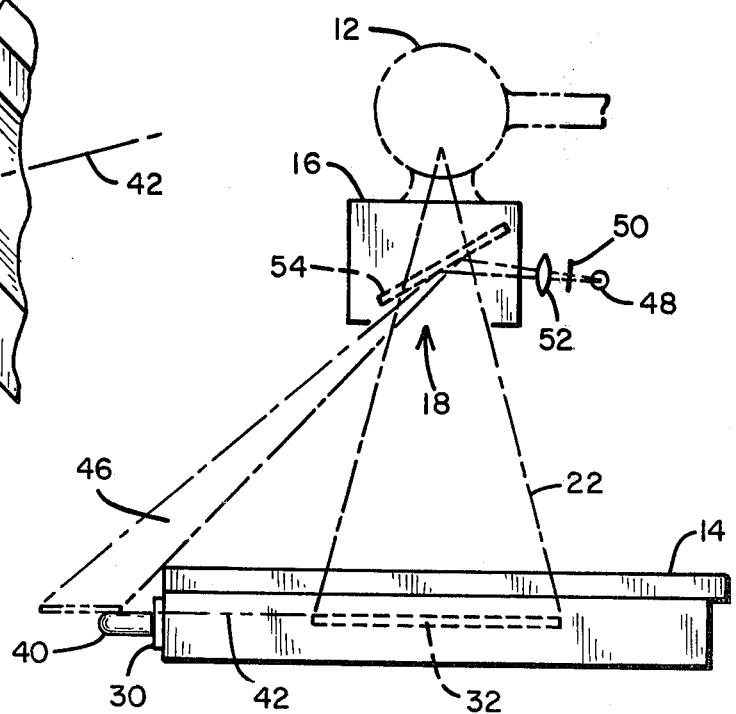
FIG. 2 is an end elevation view showing a prior art light-line system.

In addition to light localizer beam 22 it has been found helpful to provide a second beam or light-line (to be discussed in more detail with respect to FIG. 2). Prior art light-line systems have directed a beam along path 34, the shortest distance between an aperture 36 in collimator 16 and an indicator 38 on handle 40, shown in more detail in FIG. 1a. Indicator 38 is preferably a scribed or painted mark on handle 40 and fixed in alignment with a center line 42 bisecting film plane 32. It is to be understood that cassette tray 30 is ordinarily operable in a drawer like manner in a cassette tray holder or cabinet 44. In operation, cabinet 44 is moved along the long dimension of table 14 until the light-line projected along path 34 illuminates indicator 38, thus causing intersection (alignment) of film center line 42 and X-ray beam central axis 24. Intersection center line 42 and central axis 24 define a central plane of X-ray beam path 22. This condition exists when the X-ray beam path 22 is centered on the film cassette or image receptor in film plane 32.

FIG. 1 generally indicates a prior art light-line emanating from aperture 36 of collimator 16. An alternative prior art light-line system is shown in FIG. 2. Light-line beam 46 is shown terminating in a projected image that would appear if beam 46 were interrupted by a plane surface in film plane 32.

The light-line optical system of FIG. 2 includes a light bulb 48, a slit aperture plate 50, double-convex spherical lens 52, mirror 54, and aperture 18 of collimator 16. Because plate 50 has a narrow slit aperture in the plane defined by central axis 24 and center line 42, lens 52 will project a beam 46 which is relatively narrow in cross-section and which will result in a line or strip of light perpendicular to handle 40, but which due to lens 52 is relatively short in length, in the region of handle 40. In practice the length of light-lines projected by prior art systems utilizing conventional double-convex spherical lenses such as that shown at 52 will be in the range of 3-4 inches as measured along center line 42. Because of this, when the X-ray source in housing 12 is moved to a distance substantially further from film plane 32 then that shown in FIG. 2, the light-line projected by prior art systems will cease to fall upon handle 40 and be of no assistance in aligning cassette tray 30 in preparation for X-ray radiography. In addition, the light-line system of FIG. 2 is inoperative when mirror 54 is moved as is done for certain radiography techniques. Furthermore, the prior art system of FIG. 2 further reduces the length of the light-line projected by beam 46 as aperture 18 is reduced to limit the area subject to exposure during radiography techniques calling for less than the maximum able to be provided by collimator 16.

Figure 3:
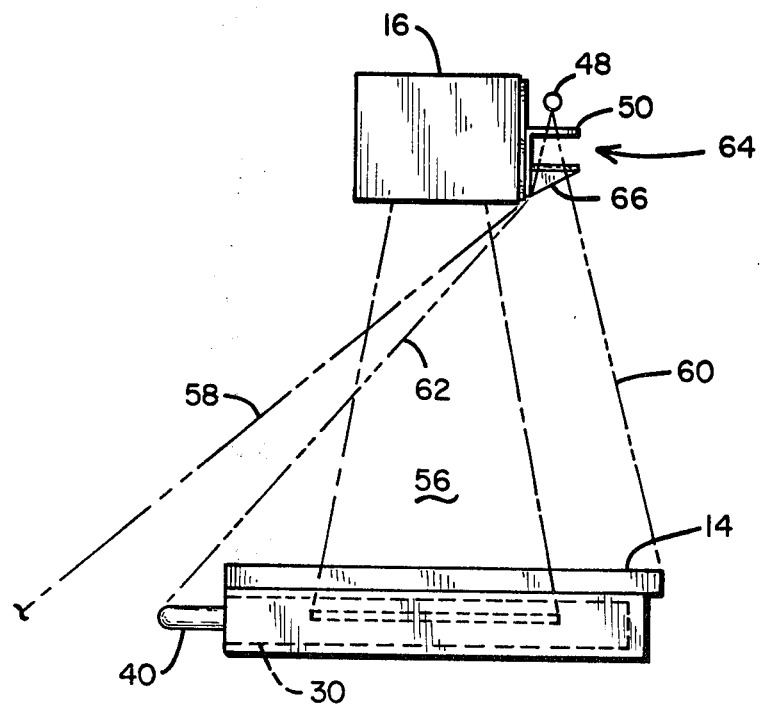
FIG. 3 is an end elevation view showing the light-line system of this invention.

Referring now more particularly to FIG. 3 the coverage of the light-line system of this invention can be seen. Collimator 16 is shown in outline for simplicity. X-ray table 14, cassette tray 30, and handle 40 are shown positioned relative to the collimator 16 at its closest normal operating distance. A light-line is projected by light-line beam 56 having boundaries 58, 60 and including line-of-sight 62 between light-line generating apparatus 64 and handle 40. Apparatus 64 may be seen to include light bulb 48, a slit aperture plate 50 and a cylindrical lens-prism combination element 66.

Figure 4:
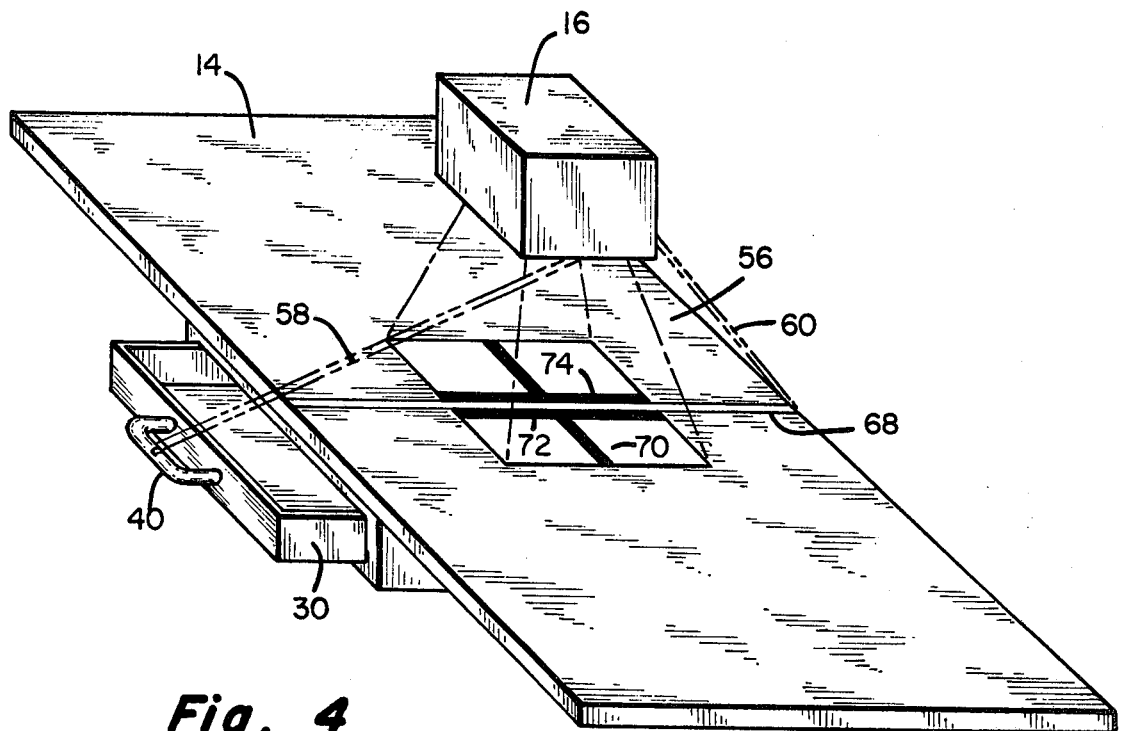
FIG. 4 is a perspective view of X-ray apparatus showing the projected images of this invention.

FIG. 4 illustrates the images projected by the light localizer and light-line beams related to the present invention. Again collimator 16 is shown positioned above X-ray table 14. Even though cassette tray 30 is shown partially extended it may be seen that light-line beam 56 continues to illuminate handle 40. In addition it may be noted that light-line image 68 extends across substantially the width of table 14, spanning light localizer image 70, and illuminating a portion of cassette tray 30 as well as handle 40. Such an extremely long, separately projected light-line is of greatly increased assistance in radiography techniques for several reasons. First, the greatly extended coverage of light-line image 68 will permit illumination of indicator 38 without regard for the spacing or distance between housing 12 and film plane 32. Next, the light-line projection system 64 is completely independent of any mirror or aperture settings within collimator 16 and thus continues to fully function in aid of radiographic alignment even if the mirror 54 is removed or the aperture 18 is set to a very small opening. Finally, even without using the light localizer beam, the light-line beam 56 will illuminate a stripe on an object or member to be radiographed and in so doing will indicate the center line or central plane of X-ray beam path 22 and thus provide an alignment aid not previously available to personnel operating the radiography equipment.

The best advantage and most frequent usage of the light-line image 68 will be in combination with light localizer image 70. The light localizer image 70 is seen to be partitioned by two symmetrical T-shaped shadows 72, 74 separated by the width of the projected light-line image 68. In the preferred embodiment, light-line image 68 is of brighter intensity than light localizer image 70. Shadows 72, 74 are preferably formed by corresponding optically-opaque and X-ray-transparent patterns on a glass plate (not shown) covering aperture 18 and secured on the lower surface of collimator 16.

Referring now to FIG. 5 an enlarged perspective view of the preferred apparatus 64 of this invention is shown mounted on the rear surface 76 (the side ordinarily furthest from X-ray equipment operator) of collimator 16. Rear surface 76 is preferably provided with a square or rectangular aperture 78 to permit light bulb or lamp 48 to serve as the source of light for the light localizing means (not shown). Surface 76 further provides a substantially plane surface suitable for locating and securing the various elements of the light-line generating appratus 64. Lamp 48 is preferably a high-intensity incandescent lamp having a filament 80 such as a quartz iodide type projection lamp (as for example a type DZE manufactured by the General Electric Company). Lamp 48 is located and secured in position by base 82 and lamp bracket 84.

Slit aperture plate 50 is preferably formed in a rectangular piece of 0.005 inches thick piece of stainless steel stock by providing for a relatively narrow, long slit aperture 85 preferably 0.015 inches wide by 0.875 inches long. Plate 50 is preferably secured to bracket 86 by means of rivets 88. Bracket 86 is preferably adjustably secured to surface 76 by means of conventional machine screws 90. Cylindrical lens-prism element 66 is preferably secured to bracket 86 by means of screws received in tapped holes in element 66 (omitted in FIG. 5, for clarity and shown in more detail in FIG. 6).

Once the various parts of apparatus 64 are assembled and adjusted, a cover 92 is affixed to the back surface 76 of collimator 16 to protect the various parts of assembly 64. Cover 92 has an aperture 94 positioned therein to permit the projection of light-line beam 56. Light-line beam 56 is characterized by parallel boundaries 58, 59 and 60, 61 and by a projected light-line image 68 as it would appear projected on a plane surface.

Referring now more particularly to FIG. 6a, a simplified view of apparatus 64 may be seen, as it would be viewed along a plane containing slit aperture 85. As shown in FIG. 6a, filament 80 and aperture 85 provide for an equivalent of a point source of light at aperture 85 when viewed in this plane. A divergent beam 96 exists between aperture 85 and upper surface 98 of element 66, whose angle of divergence is dependent upon the width and position of filament 80 with respect to aperture 85. Although it has been found to not be critical, the preferred distance from plate 80 to the center line of bulb 48 is 0.6 inches.

Upper surface 98 of element 66 forms a cylindrical lens with a cylinder axis parallel to surface 98 and spaced from it by the radius of curvature of surface 98. The cylinder axis of surface 98 is in the plane containing slit aperture 85 and preferably with parallelism between slit aperture 85 and the cylinder axis for surface 98. Since surface 98 is cylindrical, and is formed of a material substantially transparent to visible light, preferably acrylic plastic, lenticular, or lens-like surface 98 forms a cylindrical lens to collimate diverging beam 96 into parallel-sided beam 56. To accomplish this, the distance D and radius of curvature of lenticular surface 98 must be cooperatively designed to refract the boundaries of diverging beam 96 into parallel paths. In a preferred embodiment of this invention, it has been found desirable to have a radius of curvature for surface 98 of 0.75 inches and to space surface 98 from the lower surface 100 of plate 50 a distance D of 1.500 inches. It is to be unerstood that other geometries may be selected to achieve optical collimation of diverging beam 96 into a parallel sided beam 56.

It has been found that the objectives of this light-line system are achieved with a beam 56 exhibiting less than perfectly parallel sides (i.e. ideal optical collimation). Accordingly, it is to be understood that a beam 56 approaching but not reaching ideal optical collimation is to be considered "collimated".

Referring now to both FIGS. 6a and 6b, threaded or tapped holes 102 are shown in more detail as the preferred means by which element 66 is secured to bracket 86 (by means of flathead machine screws, not shown). Referring now more particularly to FIG. 6a, it has been found that various angles of a conventional prism may be utilized to deflect beam 56 in a manner to accomplish the desired projection of light-line image 68 and to position image 68 to properly illuminate X-ray table 14 and indicator 38 on handle 40 of cassette tray 30. In the preferred embodiment, prism angle A 104 is selected to be 25°, and the collimation and deflection of the light-line beam is accomplished in a combined cylindrical lens-prism optical element 66.

Element 66 is further characterized in its preferred form as being formed by a monolithic block of acrylic plastic and formed by having a principal upper plane 67, intersected by the cylindrical lens upper surface 98. Element 66 is still further characterized as having a principal lower plane 69, which together with plane 67 forms the prism angle A 104.

Apparatus 64 is preferably installed by loosely engaging screws 90 and positioning bracket 86 to obtain the pattern illustrated in FIG. 6a within prism element 66, and in addition to project light-line image 68 so as to bisect light localizer image 70 (as shown in FIG. 4). Screws 90 are then securely tightened to preserve alignment.

It is to be understood that the invention is not to be taken as limited to all of the details thereof as modifications and variations thereof may be made without departing from the spirit or scope of the invention.

What is claimed is:

1. A light-line system for visual alignment of an X-ray source with an object to receive X-rays preparatory to radiography comprising:
    a source of visible light;
    a visible light aperture means having a slit-type aperture therein for transmitting a beam of light therethrough; and
    visible light collimating means receiving and collimating said beam of visible light by directing said beam within a central plane such that two sides of said beam are substantially parallel to said central plane to produce a narrow width light-line having a useful length greatly in excess of said width.

2. The system of claim 1 wherein said collimating means comprises a cylindrical lens having a first surface comprising a convex cylindrical surface facing said slit-type aperture for receiving and collimating said beam of visible light.

3. The system of claim 2 wherein said collimating means further comprises a visible light prism which redirects said beam within said central plane.

4. The system of claim 1 wherein said collimating means comprises an optically transparent solid having a lenticular cylindrical first exterior surface for receiving and collimating said visible light and a second exterior surface at an acute angle to said first exterior surface for deflecting and projecting said narrow light-line.

5. The system of claim 1 wherein said collimating means comprises a solid having substantial transparency to visible light and having first and second refracting surfaces each having a respective principal plane wherein said first refracting surface comprises a convex cylindrical surface to collimate said visible light and said first and second refracting surfaces are oriented to each other such that their respective principal planes intersect at an acute angle.

6. The system of claim 5 wherein said second surface is substantially planar.

7. A light-line system for visually positioning an X-ray source and an article to be radiographed in combination with an X-ray collimating and light localizing means comprising:
    a source of visible light;
    a light localizing means for projecting a light localizer beam having four edges in rectangular cross-section and projecting a visible light localizer image having spaced parallel shadows centered within said localizer image; and
    a light line projecting means for projecting a light-line image bisecting said localizer image and having a length at least as long as one edge of the rectangular cross section of said light localizer image such that said light-line image is parallel to and centered between said parallel shadows in a spaced, parallel relationship to one of the rectangular cross-section edges of said light localizer beam.

8. An X-ray radiography aiming system utilizing a single source of visible light for orienting an X-ray source, a member to be radiographed and an image receptor comprising:
    an X-ray source;
    a single source of visible light;
    collimator means mounted in spaced relation to said X-ray source and operative to:
        i. collimate an X-ray beam emitted by said X-ray source,
        ii. provide a mounting for said single source of visible light, and
        iii. provide a visual indication of the path of said X-ray beam by projecting a beam of light corresponding in cross section to said X-ray beam from said single source of visible light to enable positioning of the member to be radiographed and the image receptor in the path of said X-ray beam; and
    light-line means mounted in fixed relation to said collimator means exterior to the path of said X-ray beam within said collimator and operative to provide a visual indication of a central plane of said X-ray beam path by projecting a generally planar beam of light bisecting said X-ray beam path and extending substantially across the full width of said X-ray beam path from said single source of visible light whereby said planar beam is unaffected by the cross-section setting of said collimator.

9. The aiming system of claim 8 wherein:

i. said image receptor is received in a receptor mounting means having a center-line indicator available for illumination; and ii. said planar beam of light illuminates said indicator when said X-ray beam path is centered on said image receptor.

10. A method of producing a visible light-line beam for radiography alignment comprising the steps of:

1. actuating a source of visible light;
2. generating a diverging visible light beam having at least two sides by transmitting said light through a slit-type aperture;
3. collimating said diverging beam of light transmitted through said aperture into a beam having two parallel sides by passing said beam through a cylindrical lens having a cylinder axis; and
4. deflecting said parallel-sided beam to produce a light-line by passing said parallel-sided beam through a prism such that said parallel-sided beam is projected in a plane containing said slit-type aperture and said cylinder axis.

11. The method of claim 10 wherein step 3 further comprises collimating said two sides into substantial parallelism by orienting said cylindrical lens such that its cylinder axis lies in a plane containing said slit-type aperture and said source of visible light.

12. The method of claim 11 wherein step 4 further comprises deflecting said parallel-sided beam through a prism having a prism angle aligned within the plane containing said slit-type aperture and said cylinder axis.

* * * * *